United States Patent [19]

Grollier

[11] Patent Number: 5,567,702
[45] Date of Patent: Oct. 22, 1996

[54] COMBINATION OF PYRIMIDINE DERIVATIVES AND RETINOIDS, AS SEPARATE COMPONENTS, FOR INDUCING AND STIMULATING HAIR GROWTH AND REDUCING ITS LOSS

[75] Inventor: Jean F. Grollier, Paris, France

[73] Assignee: L'Oreal, Paris, France

[21] Appl. No.: 461,843

[22] Filed: Jun. 5, 1995

Related U.S. Application Data

[63] Continuation of Ser. No. 220,582, Mar. 31, 1994, abandoned, which is a continuation of Ser. No. 614,676, Nov. 13, 1990, abandoned, which is a continuation of Ser. No. 208,136, Jun. 17, 1988, abandoned.

Foreign Application Priority Data

Aug. 12, 1987 [LU] Luxembourg .............................. 86.969

[51] Int. Cl.⁶ .......................... A61K 31/505; A61K 7/06
[52] U.S. Cl. ........................ 514/256; 424/70.1; 514/880
[58] Field of Search ...................... 424/70.1; 514/256, 514/880

[56] References Cited

U.S. PATENT DOCUMENTS

| | | | |
|---|---|---|---|
| 4,126,698 | 11/1978 | Gander et al. | 514/549 |
| 4,139,619 | 1/1979 | Chidsey, III | 424/45 |
| 4,190,594 | 1/1980 | Gander et al. | 514/859 |
| 4,194,007 | 3/1980 | VanScott et al. | 514/859 |

FOREIGN PATENT DOCUMENTS

| | | |
|---|---|---|
| 8302558 | 8/1983 | WIPO. |
| 8600616 | 1/1986 | WIPO. |

OTHER PUBLICATIONS

Conn, Current Therapy, 1981, p. 662.
Rakel, Current Therapy, 1984, pp. 599–603.

*Primary Examiner*—Shelley A. Dodson
*Attorney, Agent, or Firm*—Jacobson, Price, Holman & Stern, PLLC

[57] ABSTRACT

Combination of pyrimidine derivatives and retinoids, as separate components, for inducing and stimulating hair growth and reducing its loss.

Combination designed to induce and stimulate hair growth and reduce its loss, characterized in that it comprises in separated form:

a) a component (A) containing at least one retinoid in a physiologically acceptable medium, and b) a component (B) containing at least one pyrimidine derivative in a physiologically acceptable medium.

26 Claims, No Drawings

COMBINATION OF PYRIMIDINE DERIVATIVES AND RETINOIDS, AS SEPARATE COMPONENTS, FOR INDUCING AND STIMULATING HAIR GROWTH AND REDUCING ITS LOSS

This is a continuation of application Ser. No. 08/220,582, filed Mar. 31, 1994, abandoned, which is a continuation of application Ser. No. 07/614,676, filed Nov. 13, 1990, abandoned, which is a continuation of application Ser. No. 07/208,136, filed Jun. 17, 1988, abandoned.

The invention relates to the combination of pyrimidine derivatives and retinoids for use, successively or separated by a time interval, or to be mixed just before use for the purpose of inducing and stimulating hair growth and reducing its loss.

Man has a total of 100,000 to 150,000 hairs, and it is normal to lose 50 to 100 hairs daily. The maintenance of this total results essentially from the fact that the life of a hair is subjected to a cycle, known as the piliary cycle, during which the hair forms, grows and is shed, before being replaced by a new hair which appears in the same follicle.

Three successive phases are observed during a piliary cycle, namely, the anagen phase, the catagen phase and the telogen phase.

During the first, so-called anagen, phase, the hair passes through a period of active growth associated with intense metabolic activity at bulb level.

The second, so-called catagen phase, is transitory, and is marked by a slowing of the mitotic activities. During this phase, the hair undergoes development, the follicle atrophies and its dermal implantation is seen to be at an increasingly higher level.

The terminal, so-called telogen phase, corresponds to a period of rest of the follicle, and the hair is finally shed, pushed by a newly formed anagen hair.

This process of continuous physical renewal undergoes a natural change during ageing, the hairs becoming finer and their cycles shorter.

Alopecia occurs when this process of physical renewal is accelerated or disturbed, that is to say the growth phases are shortened, the transition of the hairs to the telogen phase takes place earlier and the hairs are shed in larger numbers. Successive growth cycles culminate in steadily finer and steadily shorter-hairs, gradually converting to an unpigmented down which can lead to baldness.

The piliary cycle is, moreover, dependent on many factors which can bring about more or less marked alopecia. Among these factors, dietary, endocrine and nervous factors may be mentioned.

Compositions that enable the effects of alopecia to be abolished or reduced, and in particular that enable hair growth to be induced or stimulated and its loss reduced, have been sought for many years in the cosmetics or pharmaceutical industry.

It has been sought, in particular, to prolong the anagen phase of the piliary cycle with respect to the telogen phase which, as described above, leads to hair loss.

Application WO-A-8,302,558 already describes compositions based on retinoids and on 2,4-diamino-6-piperidinopyrimidine 3-oxide, also known by the name minoxidil, which are used, in particular, for increasing the growth of human hair and treating certain types of alopecia.

The Applicant has discovered that it was possible, surprisingly, to improve the effect of induction and stimulation of hair growth and the reduction in its loss by applying the retinoid and the pyrimidine derivative in separate stages.

The subject of the invention is hence a combination of pyrimidine derivatives and retinoids, designed to be used successively or separated by a period of time, for inducing or stimulating hair growth and reducing its loss.

Other subjects of the invention will become apparent on reading the description and the examples which follow.

The combination according to the invention is essentially characterized in that it comprises:

a) a component A containing, in a physiologically acceptable medium, at least one retinoid, and b) a component B containing, in a physiologically acceptable medium, at least one pyrimidine derivative corresponding to the formula:

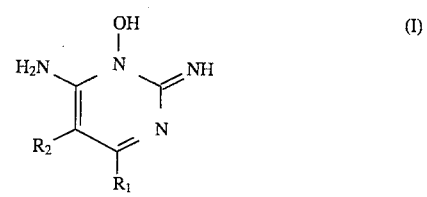

in which $R_1$ denotes a group

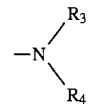

in which $R_3$ and $R_4$ may be chosen from hydrogen and a lower alkyl, alkenyl, alkylaryl or cycloalkyl group, it also being possible for $R_3$ and $R_4$ to form a heterocycle with the nitrogen atom to which they are attached, chosen, inter alia, from aziridinyl, azetidinyl, pyrrolidinyl, piperidyl, hexahydroazepinyl, heptamethylenimine, octamethylenimine, morpholine and 4-(lower alkyl)piperazinyl groups, it also being possible for the heterocyclic groups to be substituted on the carbon atoms with one to three lower alkyl groups or hydroxy or alkoxy groups; and the group $R_2$ is chosen from hydrogen and a lower alkyl, alkenyl, alkylalkoxy, cycloalkyl, aryl, alkylaryl, arylalkyl, alkylarylalkyl, alkoxyarylalkyl or haloarylalkyl group; as well as the addition salts with physiologically acceptable acids. The components A and B are designed to be used separately or separated by a time interval, for the purpose of inducing and stimulating hair growth and reducing its loss. They may also be mixed when required immediately before use.

In the combination according to the invention, for the compounds of formula (I), and alkyl or alkoxy group preferably denotes a group having 1 to 4 carbon atoms; an alkenyl group preferably denotes a group having 2 to 5 carbon atoms; aryl preferably denotes phenyl and cycloalkyl preferably denotes a group having 4 to 6 carbon atoms.

Preferred compounds consist of compounds in which $R_2$ denotes hydrogen, $R_1$ denotes a group

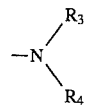

in which $R_3$ and $R_4$ form a piperidyl ring, as well as their salts such as, for example, the sulphate. Among these compounds, the especially preferred compound consists of 6-amino-1,2-dihydro-1-hydroxy-2-imino-4-piperidinopyrimidine, also known as minoxidil.

Retinoids are compounds known per se, and may be defined by the following general formula:

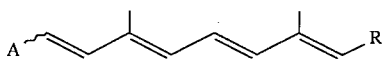 (II)

in which:

(a) A is a group chosen from the groups of formulae:

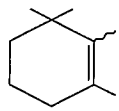 (IIIa)

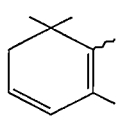 (IIIb)

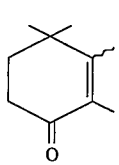 (IV)

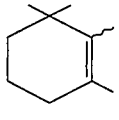 (V)

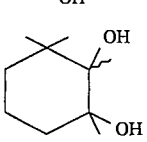 (VI)

when A denotes a group of formula (IIIa) R is chosen from the following groups:
CHO; $CH_2OR_5$,
in which $R_5$ denotes hydrogen or $C_1$–$C_4$ lower alkyl;
a group

where $R_6$ denotes $C_1$–$C_{16}$ linear or branched alkyl, $CH_2SR_7$, in which $R_7$ denotes hydrogen or methyl;

in which X denotes:

(i) OH;

(ii) $OR_8$, where $R_8$ denotes a $C_1$–$C_{15}$ alkyl radical, a $C_1$–$C_4$ arylalkyl radical optionally substituted on the aryl group, a $C_1$–$C_4$ arylcarboxyalkyl radical optionally substituted on the aryl group, or a $C_1$–$C_4$ hydroxyalkyl or $C_1$–$C_4$ amidoalkyl group;

(iii) $NR_9R_{10}$, in which $R_9$ or $R_{10}$, which may be identical or different, denotes hydrogen, $C_1$–$C_6$ alkyl, $C_1$–$C_4$ hydroxyalkyl or optionally substituted aryl;
it being possible for $R_9$ or $R_{10}$ to denote an optionally substituted heterocycle or to form, together with the nitrogen atom to which they are attached, a heterocycle which is itself optionally substituted;

(iv) an $N_3$ group;
or alternatively a group of formula $CH_2NHR_{11}$, in which $R_{11}$ denotes an optionally substituted benzoyl radical;

when A denotes a group of formula (IIIb), (IV), (V) or (VI), R denotes COOH as well as its salified or esterified form;

(b) A is a group chosen from aryl or substituted aryl groups, a heterocycle or a substituted heterocycle, an arylheterocyclic group optionally substituted on the heterocycle or an arylhomocyclic group optionally substituted on the aromatic ring, R in this case denoting a COOH group or a group $COOR_{12}$, where $R_{12}$ denotes a $C_1$–$C_4$ alkyl radical or alternatively an amide group substituted with a $C_1$–$C_4$ alkyl group, as well as their physiologically acceptable salts and esters.

In the abovementioned formula, $C_1$–$C_4$ alkyl preferably denotes methyl, ethyl, n-butyl, t-butyl; $C_1$–$C_{16}$ alkyl preferably denotes ethyl, propyl, palmityl; aryl preferably denotes phenyl or benzyl, and the substituents on the aryl groups are preferably $C_1$–$C_4$ alkyl, $C_1$–$C_{12}$ alkoxy, hydroxyl, halo or nitro groups, it being possible for the alkoxy or alkyl groups themselves to be optionally substituted with an OH group.

The heterocyclic groups can be, inter alia, groups derived from phthalimide or from succinimide, or 4 to 6-membered heterocycles containing one or more oxygen atoms and one or more nitrogen atoms.

The compounds of the retinoid family defined above are chosen, in particular, from: retinal, retinol, retinyl acetate, propionate and palmitate, retinoic acid in all-trans, 13-cis, 9-cis, 11-cis, 11,13-dicis, and 9–13-dicis forms, the corresponding zinc retinoates and quaternary ammonium retinoates of formula:

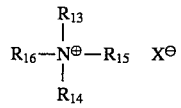 (VII)

in which $X\ominus$ denotes an all-trans- or 13-cis-retinoate radical; and (i) $R_{13}$, $R_{14}$ and $R_{15}$, which may be identical or different, denote a $C_1$–$C_4$ linear alkyl group which can bear one or more hydroxyl group(s) in the chain,
$R_{16}$ denoting a $C_{12}$–$C_{18}$ linear alkenyl or alkyl;

(ii) $R_{15}$ denotes a group:

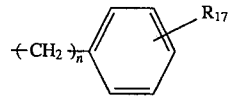

in which:
n equals 0 or 1,
$R_{17}$ denotes a hydrogen or halogen atom, a hydroxyl group, a $C_1$–$C_{18}$ hydroxyalkyl or alkyl group or a $C_2$–$C_{18}$ acyl group;
$R_{13}$, $R_{14}$ and $R_{15}$ having the meanings stated under (i)

(iii) $R_{13}$ and $R_{14}$ can form an aliphatic heterocycle optionally containing an oxygen atom, a nitrogen atom or a sulphur atom;
$R_{15}$ or $R_{16}$ having the meanings stated under (i) and (ii).

Other compounds falling within the definition of retinoids that are especially usable according to the invention are chosen from:
all-trans-retinoyloxyacetamide, a mixture of 2-hydroxy-1-propyl and 1-hydroxy-2-propyl all-trans-retinoates, 2-hydroxy-ethyl all-trans-retinoate, 4-nitrobenzyl all-trans-retinoate, benzyl all-trans-retinoate, 4-(all-trans-retinoyloxyacetyl)catechol, 2-cyclohexylethyl all-trans-retinoate, 10-carboxymethyldecyl all-trans-retinoate, 4-hydroxybutyl all-trans-retinoate, cholesteryl all-trans-retinoate, 4-bromobenzyl all-trans-retinoate, cholesteryl all-trans-retinoyloxyacetate, all-trans-retinoyloxyacetyl-benzene, 4-(all-trans-retinoyloxyacetyl)bromobenzene, 4-(all-trans-retinoyloxyacetyl)nitrobenzene, 4-all-trans-retinoloxyacetyl) benezonitrile, all-trans-retinoyloxyacetyl-2,4-dichlorobenzene, N-(all-trans-retinoyloxy)phthalimide, N-(all-trans-retinoyloxy)succinimide, 4-(all-trans-retinoyloxyacetyl)methoxybenzene, 4-(all-trans-retinoyloxyacetyl)phenol, 4-(all-trans-retinoyloxyacetyl)-3,4,5-trimethoxybenzene, 4-(all-trans-retinoyloxyacetyl)-2,4,6-trimethylbenzene, 4-(all-trans-retinoyloxyacetyl)toluene, 4-(all-trans-retinoyloxyacetyl)ethoxybenzene, 4-(all-trans-retinoyloxyacetyl)acetoxybenzene, 4-(all-trans-retinoyloxyacetyl)napththalene, 4-(all-trans-retinoyloxyacetyl)biphenyl, 4-(all-trans-retinoyloxyacetyl)-2,5-dimethoxybenzene, 1-(all-trans-retinoyloxyacetyl)-2,4-dimethylbenzene, 1-(all-trans-retinoyloxyacetyl)-3,4-diacetoxybenzene, all-trans-retinamide, 2-hydroxyethyl-all-trans-retinamide, N-ethyl-all-trans-retinamide, 4-(all-trans-retinoyl)aminophenol, N-methyldimethyldioxolane-retinamide, N-(orthocarboxyphenyl)retinamide, N-(p-carboxyphenyl)retinamide, N-hydroxypropyl-all-trans-retinamide, N-hydroxypropyl-13-cis-retinamide, N-(5-tetrazolyl)-all-trans-retinamide, N-(5-tetrazolyl)-13-cis-retinamide, N-(3,4-methylenedioxyphenylmethyl)-all-trans-retinamide, N-(n-propyl)-all-trans-retinamide, N-tert-butyl-all-trans-retinamide, N-(1,1,3,3-tetramethylbutyl)-all-trans-retinamide, N-(4-carboxymethyl-3-hydroxyphenyl)-all-trans-retinamide, N-[β-(3,4-dimethoxyphenyl)ethyl]-all-trans-retinamide, 2-(all-trans-retinoylamino)benzothiazole, 1-(all-trans-retinoyl)-1,2,4-triazole, N-(all-trans-retinoyl)imidazole, 1-nicotinoyl-2-(all-trans-retinoyl)hydrazine, N-(all-trans-retinoyl)morpholine, trans-β-ionone (all-trans-retinoyl)hydrazone, N,N'-dicyclohexyl-N-(all-trans-retinoyl)urea, acetone (all-trans-retinoyl)hydrazone, N-benzoylretinylamine and retinoyl azide.

Groups denoted by A, and defined above in paragraph (b) in connection with the aryl, substituted aryl, heterocyclic or substituted heterocyclic groups, the aryl-heterocyclic groups substituted on the heterocycle or arylhomocyclic groups substituted on the aromatic ring, are chosen, in particular, from the following groups:

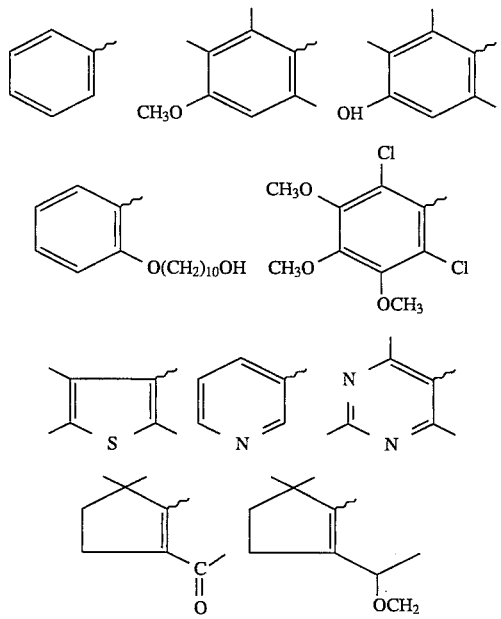

-continued

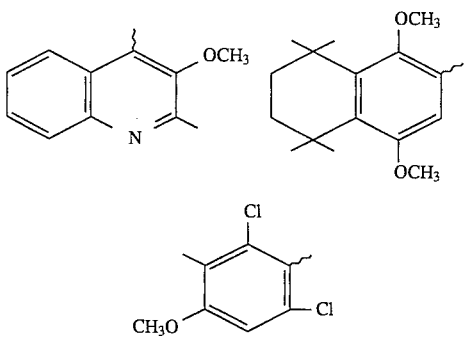

The group R can have the meanings COOH, CONHC$_2$H$_5$ and COOC$_2$H$_5$.

Especially preferred compounds in this family are motretinide and etretinate.

Other retinoids which are usable according to the invention correspond to the following formulae, or the physiologically acceptable salts or esters thereof.

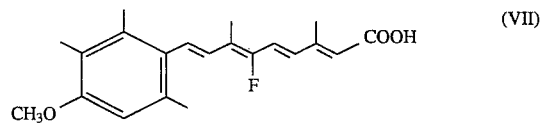 (VII)

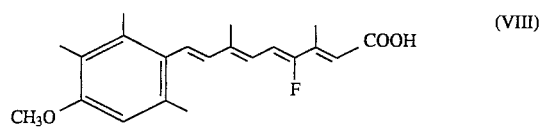 (VIII)

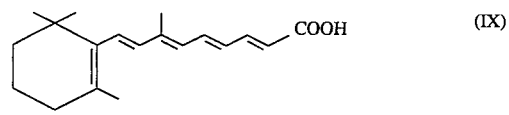 (IX)

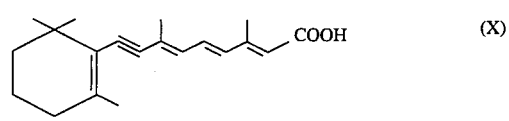 (X)

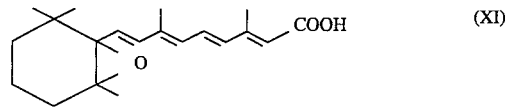 (XI)

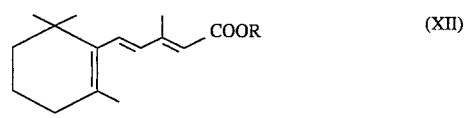 (XII)

Compounds of the retinoid family which are usable according to the invention are described, in particular, in U.S. Pat. Nos. 4,190,594 and 4,126,698, EP-A-010 209, EP-A-010 208, EP-A-097 76, French Patent 2,293,193 and EP-A-033,095.

More especially preferred retinoids according to the invention correspond to the general formula:

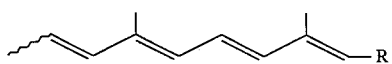

and can be in the forms of the all-trans or 13-cis isomers, in which formula the group R denotes a radical

in which X denotes OH or OY, Y denoting an alkyl group having from 1 to 15 carbon atoms, it also being possible for X to denote an amino group which is optionally mono- or disubstituted with a lower alkyl group preferably having 1 to 6 carbon atoms, R also being able to denote a —CH$_2$OH or —CHO group, and A denoting a group:

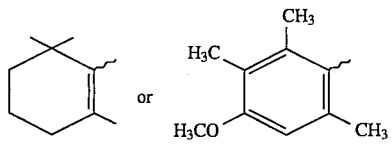

Among especially preferred derivatives, there may be mentioned the products commonly known as tretinoin, isotretinoin, retinol, motretinide and etretinate, retinol derivatives such as the acetate, palmitate-or propionate and zinc all-trans retinoate.

The components A and B used in the combination according to the invention may be presented in various forms customarily used for topical application, and more especially in the form of a lotion, optionally thickened, a gel, an emulsion or a foam optionally packaged as an aerosol.

The physiologically acceptable medium can consist of water or a mixture of water and a solvent chosen, in particular, from lower alcohols such as ethyl alcohol, isopropyl alcohol, tert-butyl alcohol, alkylene glycols and alkylene glycol or dialkylene glycol alkyl ethers.

The solvents are preferably present in proportions of between 1 and 80% by weight, relative to the total weight of the composition.

These media may be thickened using thickening agents which are known per se much as, more especially, polyacrylic acids crosslinked with a polyfunctional agent, such as products sold by the company "GOODRICH" under the name "CARBOPOL", for example CARBOPOL 910, 934, 934D, 940, 941 and 1342, or thickeners resulting from the ionic interaction of a cationic polymer, consisting of a copolymer of cellulose or a copolymer of a cellulose derivative grafted with a water-soluble quaternary ammonium monomer salt, with a carboxylic anionic polymer having an absolute capillary viscosity in dimethylformamide or methanol, at a concentration of 5% and at 30° C., of less than or equal to $30 \times 10^{-3}$ Pa.s, the thickener itself having an Epprecht-Drage, module 3, viscosity in 1% strength solution in water at 25° C. of greater than or equal to 0.5 Pa.s.

Especially preferred thickeners of this type are thickeners resulting from the ionic interaction of a copolymer of hydroxyethylcellulose grafted by a free-radical method with diallyldimethylammonium chloride, such as the products sold by the company NATIONAL STARCH under the name "CELQUAT L 200 or H 100", with copolymers of methacrylic acid with methyl methacrylate or ethyl monomaleate, butyl methacrylate or maleic acid.

Other thickening agents which also have a gelling action may be chosen from cellulose derivatives represented more especially by hydroxymethylcellulose, carboxymethylcellulose, hydroxybutylcellulose, hydroxyethylcellulose and, in particular, products sold by the company UNION CARBIDE under the name "CELLOSIZE QP and WP" those sold by the company HERCULES under the name "NATROSOL 150 and 250"; hydroxypropylcellulose such as the products sold by the company HERCULES under the name "KLUCEL" (H, HF, HP, M, EF, G); methylhydroxyethylcellulose such as the products sold by the company HOECHST under the name "TYLOSE MH 300"; and methylhydroxypropylcellulose such as the products sold by the company DOW CHEMICAL under the name "METHOCEL" (E. F. J. K).

It is also possible to use heterobiopolysaccharides such as the products synthesized by the fermentation of sugars by microorganisms containing, in particular, mannose, glucose and glucuronic or galacturonic acid units in their chains, and more especially xanthan gums having a molecular weight of between 1,000,000 and 50,000,000 or scleroglucans. There may be mentioned, in particular, products sold under the name "KELTROL T or TF", "KELZAN S", "KELZAN K9 C57", "KELZAN K8 B12" and "KELZAN K3 B130", marketed by the company KELCO; the products sold by the company RHONE-POULENC under the name "RHODOPOL 23, 23 SC", "RHODIGEL 23"; the products marketed by the company SCHONER under the name "DEUTERON XG"; and the products sold by the company CECA/SATIA under the name "ACTIGUM CX9, CS11 and C56".

These thickeners are preferably used in proportions of between 0.1 and 5% by weight, and preferably between 0.4 and 3% by weight, relative to the weight of each of the components.

The compounds according to the invention can also contain any other adjuvants customarily used in topical, cosmetic or pharmaceutical compositions, such as, more especially, preservatives, complexing agents, colourings, perfumes, alkalinizing or acidifying agents, anionic, cationic, nonionic, amphoteric surfactants or mixtures thereof, and anionic, cationic, nonionic and amphoteric-polymers, as well as mixtures thereof.

The pH of these compositions can vary between 4 and 9.

The retinoids used according to the invention can be present in the compositions used in proportions of between 0.001 and 2% by weight, and preferably between 0.01 and 0.5% by weight, relative to the total weight of the component A.

The pyrimidine derivatives of formula (I) are used in the compositions according to the invention in proportions preferably of between 0.1 and 10% by weight, and preferably between 0.1 and 3% by weight, and especially between 0.25 and 2% by weight, relative to the weight of the component B.

These derivatives can be present, either in dissolved form in the physiologically acceptable medium, or else totally or partially suspended in this medium, in particular in the form of particles having a particle size of less than 80 μ, and preferably less than 20 μ, and especially less than 5 μ.

These compositions are designed to be applied separately or separated by a time interval, in a process for treating the scalp for the purpose of inducing and stimulating hair growth and reducing its loss.

A particular embodiment consists in applying, in a first stage, the component A containing the retinoid derivative, and, after a contact time of 1 minute to 12 hours, in applying the component B containing the pyrimidine derivative of formula (I).

The application of the component A based on the retinoid derivative can preferably be performed at night, and the application of the component B containing the pyrimidine derivative is, in this instance, performed in the morning. This makes it possible, in particular, to remedy any problems which may arise as a result of photosensitization.

The applicant has found that the application of this combination in two stages was especially effective in respect of the treatment of hair loss, in particular in comparison with the application of a single composition containing the two components.

The combination according to the invention may be packaged in a multi-compartment arrangement, also known as a "kit" or outfit, in which the first compartment contains the component A based on the retinoid and the second compartment the component B based on the pyrimidine derivative of formula (I).

The combination according to the invention may preferably be applied at a dose of 0.5 to 2 cm³ of lotion of pyrimidine derivative per application.

The treatment process according to the invention may be carried out in various forms such as, for example, by applying a shampoo based on retinoid derivatives in a first stage, followed by a lotion containing the pyrimidine derivative of formula (I). It is also possible to apply one of the compositions in the form of a cream, and the other in the form of a foam.

An especially preferred implementation consists in applying the composition A in the form of a gel and in following the treatment with a rinse with a lotion containing minoxidil.

The process according to the invention is essentially directed towards the therapeutic treatment of hair loss, inasmuch as it acts on the biological functions or mechanisms at the origin of hair growth.

This process may also be considered to be a cosmetic treatment process, inasmuch as it enables the beauty of the hair to be improved by reinvigorating it and giving it a better appearance.

The examples which follow are designed to illustrate the invention without a limitation of the latter being implied.

EXAMPLE 1

There is prepared a

| COMPOSITION A | |
|---|---|
| Retinoic acid | 0.031 g |
| Butylated hydroxytoluene | 0.001 g |
| Ethyl alcohol | 95 g |
| Propylene glycol | qs 100 g |

This composition is presented in the form of a lotion.

There is prepared a

| COMPOSITION B | |
|---|---|
| Minoxidil | 0.80 g |
| Propylene glycol | 20 g |
| Ethyl alcohol | 50 g |
| Water | qs 100 g |
| pH = 8 | |

This composition is presented in the form of a lotion.

Composition A is applied in the evening and composition B in the morning. The use of composition A in the evening offers the advantage that the retinoic acid is not exposed to UV light.

Composition A can also be applied in the morning and composition B in the evening or they can be applied one after the other.

EXAMPLE 2

The composition described in Example 1 is used as composition A.

Composition B is as follows:

| Minoxidil | 0.625 g |
|---|---|
| Ethyl alcohol | 95 g |
| Propylene glycol | qs 100 g |

This composition is presented in the form of a lotion.

Composition A is applied, followed by composition B, after an interval of 30 minutes.

EXAMPLE 3

The following composition A is prepared:

| Retinoic acid | 0.025 g |
|---|---|
| Butylated hydroxytoluene | 0.020 g |
| Butylated hydroxyanisole | 0.030 g |
| Ethyl alcohol | 50 g |
| Water | 13 g |
| Carbopol 940 | 1 g |
| Triethanolamine | qs pH = 5 |
| Propylene glycol | qs 100 g |

This composition is presented in the form of a thick gel.

The following composition B is prepared:

| Minoxidil | 2.2 g |
|---|---|
| Propylene glycol | 20 g |
| Ethyl alcohol | 50 g |
| water | qs 100 g |
| pH = 8.35 | |

This composition is presented in the form of a lotion.

Composition A is applied in the evening and composition B in the morning. The compositions were also applied, one after the other, with an interval of 5 minutes.

EXAMPLE 4

The following composition A is prepared:

| Retinoic acid | 0.025 g |
|---|---|
| Butylated hydroxytoluene | 0.050 g |
| Hydroxypropylcellulose | 3 g |
| Absolute ethyl alcohol | qs 100 g |

This composition is presented in the form of a gel.

The following composition B is prepared:

| Minoxidil | 0.5 g |
|---|---|
| Hydroxypropylcellulose | 3 g |
| Ethyl alcohol | 50 g |
| Water | qs 100 g |
| pH = 7.25 | |

This composition is presented in the form of a gel.

Composition A is applied in the evening and composition B in the morning.

EXAMPLE 5

The following composition A is prepared:

| | |
|---|---|
| Retinoic acid | 0.050 g |
| DL α-tocopherol | 0.100 g |
| Ethyl alcohol | 50 g |
| Propylene glycol | qs 100 g |

The following composition B is prepared:

| | |
|---|---|
| Minoxidil | 1 g |
| Propylene glycol | 20 g |
| Ethyl alcohol | 50 g |
| Water | qs 100 g |
| pH = 8.3 | |

Composition A and composition B are applied successively after a time of exposure to composition A of 1 hour.

EXAMPLE 6

The following two compositions A and B are prepared, packed as a kit:

| COMPOSITION A | |
|---|---|
| Retinoic acid | 0.062 g |
| Butylated hydroxytoluene | 0.025 g |
| Ethyl alcohol | 95 g |
| Propylene glycol | qs 100 g |
| COMPOSITION B | |
| Minoxidil | 1.25 g |
| Ethyl alcohol | 95 g |
| Propylene glycol | qs 100 g |

At the time of use, a mixture of an equal weight of composition A and of composition B is prepared and this extemporaneous mixture is applied to the areas to be treated.

EXAMPLE 7

The following compositions A and B are prepared, which are packed as a kit:

| COMPOSITION A | |
|---|---|
| Retinoic acid | 0.375 g |
| Butylated hydroxytoluene | 0.025 g |
| Ethyl alcohol | 95 g |
| Propylene glycol | 100 |
| COMPOSITION B | |
| Minoxidil | 2.2 g |
| Propylene glycol | 20 g |
| Ethyl alcohol | 50 g |
| Water | qs 100 g |

At the time of use, 0.4 g of composition A and 5.06 g of composition B are mixed and this extemporaneous mixture is applied to the areas to be treated at a dosis of 1 g per day.

The retinoic acid used in Examples 1 to 7 is the form of acid which is usually sold under the name tretinoin or all-trans retinoic acid.

EXAMPLE 8

The following two compositions A and B are prepared, which are packed as a kit:

| COMPOSITION A | |
|---|---|
| Zinc retinoate | 0.05 g |
| Hydroxypropylcellulose, sold under the trade name KLUCEL G by the HERCULES Company | 3 g |
| Butylated hydroxytoluene | 0.1 g |
| Ethyl alcohol | qs 100 g |

This composition A is presented in the form of a gel.

| COMPOSITION B | |
|---|---|
| Minoxidil | 2.2 g |
| Propylene glycol | 20 g |
| Ethyl alcohol | 50 g |
| Water | qs 100 g |

The two compositions A and B are applied separately or separated by a period of time, either one after the other, either A in the morning and B in the evening or vice versa, or with a time interval of between 5 minutes and a few hours.

EXAMPLE 9

The following two compositions A and B are prepared, which are packed as a kit:

| COMPOSITION A | |
|---|---|
| 13-Cis retinoic acid | 0.025 g |
| Ethyl alcohol | 43.2 g |
| Butylated hydroxytoluene | 0.025 g |
| Polyethylene glycol 400 | qs 100 g |
| COMPOSITION B | |
| Minoxidil | 2.2 g |
| Propylene glycol | 20 g |
| Ethyl alcohol | 50 g |
| Water | qs 100 g |

The two compositions A and B are applied separated by a period of time, namely B in the morning and A in the evening.

EXAMPLE 10

The two following compositions A and B are prepared, which are packed as a kit:

| COMPOSITION A | |
|---|---|
| Retinyl palmitate | 0.055 g |
| DL α-tocopherol | 0.05 g |
| Ethyl alcohol | 95 g |
| Propylene glycol | qs 100 g |
| COMPOSITION B | |
| Minoxidil | 2.2 g |
| Propylene glycol | 20 g |
| Ethyl alcohol | 50 g |
| Water | qs 100 g |

The two compositions A and B are applied separately or separated by a period of time, namely, either one after the other, either A in the morning and B in the evening or vice versa, or with an interval of between 5 minutes and a few hours.

EXAMPLE 11

The following two compositions A and B are prepared, which are packed as a kit:

| COMPOSITION A | |
|---|---|
| Zinc retinoate | 0.1 g |
| Ethyl alcohol | 43 g |
| Polyethylene glycol 400 | qs 100 g |
| COMPOSITION B | |
| Minoxidil | 2.2 g |
| Propylene glycol | 20 g |
| Ethyl alcohol | 50 g |
| Water | qs 100 g |

The two compositions A and B are applied separately or separated by a period of time, namely, either one after the other, either A in the morning and B in the evening or vice versa, or with a time interval of between 5 minutes and a few hours.

EXAMPLE 12

The following compositions are prepared:

| COMPOSITION A | |
|---|---|
| All-trans retinoic acid | 0.031 g |
| Butylated hydroxytoluene | 0.0125 g |
| Ethanol/propylene glycol (95:5) | qs 100 g |
| COMPOSITION B | |
| 2,4-diamino-6-diethylaminopyrimidine 3-oxide | 2.5 g |
| Propylene glycol | 20 g |
| Ethanol | 50 g |
| Water | qs 100 g |

2 g of composition A are applied in the morning and 2 g of composition B are applied in the evening to the alopecic areas, every day for 2 to 3 months.

EXAMPLE 13

The following compositions are prepared:

| COMPOSITION A | |
|---|---|
| 13-Cis-hexadecyltrimethylammonium retinoate | 0.15 g |
| Butylated hydroxytoluene | 0.05 g |
| Anhydrous ethanol | qs 100 g |
| COMPOSITION B | |
| Minoxidil | 1.5 g |
| Ethanol/propylene glycol (95:5) | qs 100 g |

This two-part composition is applied in a similar manner to the one indicated for Example 12, and makes it possible, following 2 to 3 months' treatment, to markedly slow down hair loss.

I claim:

1. A method for inducing and stimulating hair growth and for decreasing hair loss or for improving the appearance of the hair, comprising applying first and second components to the scalp, successively or intermittently, each component being in lotion, thickened lotion or gel form, wherein the first component (A) comprises a physiologically acceptable medium and 0.001 to 2% by weight relative to the weight of component (A) of at least one retinoid selected from the group consisting of compounds of formula:

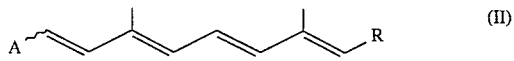

wherein

A is a substituent selected from groups of formulae:

and

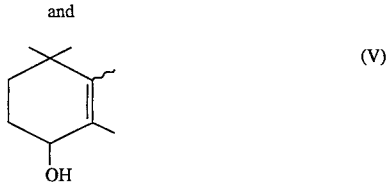

and wherein R is selected such that:

when A is a group of formula (IIIb), (IV) or (V), R is COOH;

when A is a group of formula (IIIa), R is selected from the group consisting of CHO, $CH_2OR_5$ in which $R_5$ is hydrogen or $C_1$–$C_4$ lower alkyl,

in which $R_6$ denotes $C_1$–$C_{16}$ linear or branched alkyl, $CH_2SR_7$ in which $R_7$ is hydrogen or methyl and

in which X is selected from the group consisting of
  (i) OH,
  (ii) $OR_8$ in which $R_8$ denotes a $C_1$–$C_4$ alkyl radical, an unsubstituted $C_1$–$C_4$ arylalkyl radical, a $C_1$–$C_4$ arylalkyl radical substituted on the aryl group, an unsubstituted $C_1$–$C_4$ arylcarboxyalkyl radical, a $C_1$–$C_4$ arylcarboxyalkyl radical substituted on the aryl group, or a $C_1$–$C_4$ hydroxyalkyl or $C_1$–$C_4$ amidoalkyl group;

(b) retinoids selected from the group consisting of compounds of formula (II) in which R is COOH, $CONHC_2H_5$ or $COOC_2H_5$ and A is selected from the group consisting of

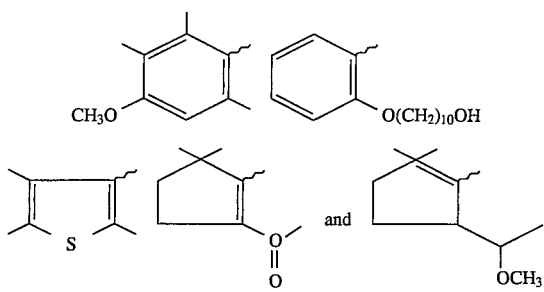

(c) retinoids selected from the group consisting of compounds of the formulae:

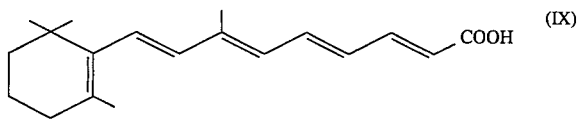

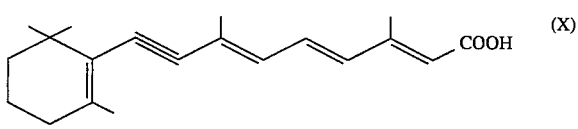

and the second component (B) comprises a physiologically acceptable medium and 0.1 to 3% by weight relative to the weight of component (B) of at least one pyrimidine derivative having the formula:

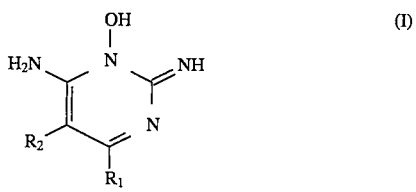

or an acid addition salt thereof, wherein $R_1$ represents a group having the formula

wherein each of $R_3$ and $R_4$ is a member selected from the group consisting of hydrogen, lower alkyl, alkenyl, alkylaryl and cycloalkyl, the alkyl part of which is a lower alkyl radical, or $R_3$ and $R_4$ with the nitrogen to which each is bound, form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidino, hexahydrolazepinyl, heptamethylenimino, octamethylenimino, morpholine and 4-(lower alkyl)piperazinyl, and wherein $R_2$ is a member selected from the group consisting of hydrogen, lower alkyl, alkenyl, alkoxyalkyl, cycloalkyl, aryl, alkylaryl, arylalkyl, alkylarylalkyl, alkoxyarylalkyl and haloarylallkyl, the alkyl part of which is a lower alkyl radical.

2. The method of claim 1, wherein said pyrimidine derivative of formula (I) is a member selected from the group consisting of a compound in which $R_2$ is hydrogen and $R_1$ is a group having the formula

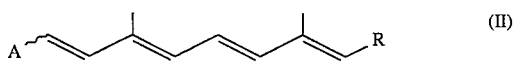

in which $R_3$ and $R_4$ form a piperidyl ring.

3. The method of claim 1, wherein said retinoid is selected from the group consisting of compounds of formula:

wherein

A is a substituent selected from the group consisting of unsubstituted aryl groups, substituted aryl groups, unsubstituted heterocyclic groups, substituted heterocyclic groups, unsubstituted arylheterocyclic groups, arylheterocyclic groups that are substituted on the heterocycle, unsubstituted arylhomocyclic groups, arylhomocyclic groups that are substituted on the aromatic ring, and groups of formulae:

and

and wherein R is selected such that:
when A is a group of formula (IIIb), (IV), (V) or (VI), R is COOH;
when A is a group of formula (IIIa), R is selected from the group consisting of CHO, $CH_2OR_5$ in which $R_5$ is hydrogen or $C_1$–$C_4$ lower alkyl,

in which $R_6$ denotes $C_1$–$C_{16}$ linear or branched alkyl, $CH_2SR_7$ in which $R_7$ is hydrogen or methyl and

in which X is selected from the group consisting of (i) OH, (ii) OR$_6$ in which R$_6$ denotes a C$_1$–C$_4$ alkyl radical, an unsubstituted C$_1$–C$_4$ arylalkyl radical, a C$_1$–C$_4$ arylalkyl radical substituted on the aryl group, an unsubstituted C$_1$–C$_4$ arylcarboxyalkyl radical, a C$_1$–C$_4$ arylcarboxyalkyl radical substituted on the aryl group, or a C$_1$–C$_4$ hydroxyalkyl or C$_1$–C$_4$ amidoalkyl group;

(iii) NR$_9$R$_{10}$ in which R$_9$ and R$_{10}$, which may be identical or different, are substituents selected from the group consisting of hydrogen, C$_1$–C$_4$ alkyl, C$_1$–C$_4$ hydroxyalkyl unsubstituted aryl, substituted aryl, an unsubstituted heterocycle and a substituted heterocycle or R$_9$ and R$_{10}$ form, together with the nitrogen atom to which each is attached, a heterocycle which is itself unsubstituted or substituted;

(iv) an N$_3$ group or a group of formula CH$_2$NHR$_{11}$, in which R$_{11}$ is an unsubstituted or substituted benzoyl radical;

and when A is a group selected from the group consisting of unsubstituted aryl groups, substituted aryl groups, unsubstituted heterocyclic groups, substituted heterocyclic groups, unsubstituted arylheterocyclic groups, arylheterocyclic groups substituted on the heterocycle, unsubstituted arylhomocyclic groups, arylhomocyclic groups substituted on the aromatic ring, R is a COOH group or a COOR$_{12}$ group in which R$_{12}$ is selected from the groups consisting of a C$_1$–C$_4$ alkyl radical, an amide group that is substituted with a C$_1$–C$_4$ alkyl group, and physiologically acceptable salts and esters thereof.

4. The method of claim 1, wherein said retinoid is a member selected from the group consisting of retinal, retinol, retinyl acetate, propionate and palmitate, retinoic acid in all-trans, 13-cis, 9-cis, 11-cis or 9,13-dicis forms of retinoic acid, the corresponding zinc retinoates and quaternary ammonium retinoates of formula:

in which X denotes an all-trans- or 13-cis-retinoate radical and R$_{13}$, R$_{14}$, R$_{15}$ and R$_{16}$ are either (i), (ii) or (iii), wherein (i) R$_{13}$, R$_{14}$ and R$_{15}$, which may be identical or different, denote a C$_1$–C$_4$ linear alkyl group which can bear one or more hydroxyl group(s) in the chain, R$_{16}$ denotes a C$_{12}$–C$_{18}$ linear alkenyl or alkyl;

(ii) R$_{15}$ denotes a group:

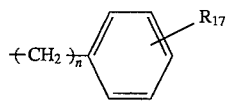

in which:

n equals 0 or 1,

R$_{17}$ denotes a hydrogen or halogen atom, a hydroxyl group, a C$_1$–C$_{18}$ hydroxyalkyl or alkyl group or a C$_2$–C$_{18}$ acyl group;

R$_{13}$, R$_{14}$ and R$_{15}$ can form an aliphatic heterocycle optionally containing an oxygen atom, a nitrogen atom or a sulphur atom;

R$_{15}$ or R$_{16}$ having the meanings stated under (i) and (ii), all-trans-retinoyloxyacetamide, the mixture of 2-hydroxy-1-propyl and 1-hydroxy-2-propyl all-trans-retinoates, 2-hydroxy-ethyl all-trans-retinoate, 4-nitrobenzyl all-trans-retinoate, benzyl all-trans-retinoate, 4-(all-trans-retinoyloxy-acetyl)catechol, 2-cyclohexylethyl all-trans-retinoate, 10-carboxymethyldecyl all-trans-retinoate, 4-hydroxybutyl all-trans-retinoate, cholesteryl all-trans-retinoate, 4-bromobenzyl all-trans-retinoate, cholesteryl all-trans-retinoyloxyacetate, all-trans-retinoyloxyacetyl-benzene, 4-(all-trans-retinoyloxyacetyl) bromobenzene, 4-(all-trans-retinoyloxyacetyl)nitrobenzene, 4-(all-trans-retinoyloxyacetyl) benezonitrile, all-trans-retinoyloxy-acetyl-2,4-dichlorobenzene, N-(all-trans-retinoyloxy)-phthalimide, N-(all-trans-retinoyloxy)succinimide, 4-(all-trans-retinoyloxyacetyl) methoxybenzene, 4-(all-trans-retinoyloxyacetyl)phenol, 4-(all-trans-retinoyloxyacetyl)-3,4,5-trimethoxybenzene, 4-(all-trans-retinoyloxyacetyl)-2,4,6-trimethylbenzene, 4-(all-trans-retinoyloxyacetyl)-toluene, 4-(all-trans-retinoyloxyacetyl)ethoxybenzene, 4-(all-trans-retinoyloxyacetyl)acetoxybenzene, 4-(all-trans-retinoyloxyacetyl)naphthalene, 4-(all-trans-retinoyloxyacetyl)biphenyl, 4-(all-trans-retinoyloxyacetyl)-2, 5-dimethoxybenzene, 1-(all-trans-retinoyloxyacetyl)-2,4-dimethylbenzene, 1-(all-trans-retinoyloxyacetyl)-3,4-diacetoxybenzene, all-trans-retinamide, 4-(all-trans-retinoyl)amino-phenol, N-methyldimethyldioxolane-retinamide, N-(orthocarboxyphenyl)retinamide, N-(p-carboxyphenyl)retinamide, N-hydroxypropyl-all-trans-retinamide, N-hydroxypropyl-13-cis-retinamide, N-(5-tetrazolyl)-all-trans-retinamide, N-(5-tetrazolyl)-13-cis-retinamide, N-(3,4-methylenedioxyphenylmethyl)-all-trans-retinamide, N-n-propyl-all-trans-retinamide, N-tert-butyl-all-trans-retinamide, N-1,1,3,3-tetramethylbutyl)-all-trans-retinamide, N-(4-carboxymethyl-3-hydroxyphenyl)-all-trans-retinamide, N-(4-carboxymethyl-3-hydroxyphenyl)-all-trans-retinamide, N-[β-(3,4-dimethoxyphenyl)ethyl]-all-trans-retinamide, 2-(all-trans-retinoylamino)benzothiazole, 1-(all-trans-retinoyl)-1,2, 4-triazole, N-(all-trans-retinoyl)imidazole, 1-nicotinoyl-2-(all-trans-retinoyl)hydrazine, N-(all-trans-retinoyl)morpholine, trans-β-ionone (all-trans-retinoyl)hydrazone, N,N'-dicyclohexyl-N-(all-trans-retinoyl)urea, acetone (all-trans-retinoyl)hydrazone, N-benzoylretinylamine and retinoyl azide.

5. The method of claim 1, wherein said retinoid is a compound of formula

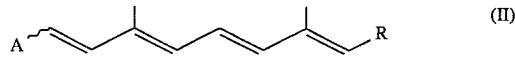

in which R is COOH, CONHC$_2$H$_5$ or COOC$_2$H$_5$ and A is selected from the group consisting of

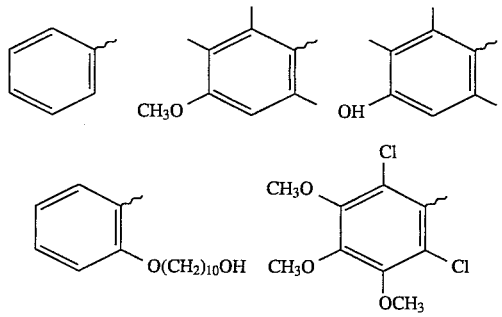

-continued

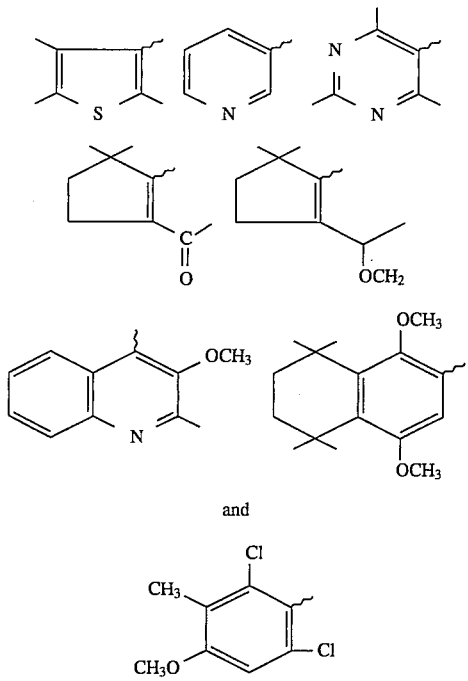

and

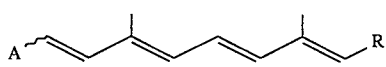

6. The method of claim 1, wherein said retinoid is a member selected from the group consisting of compounds of the formula:

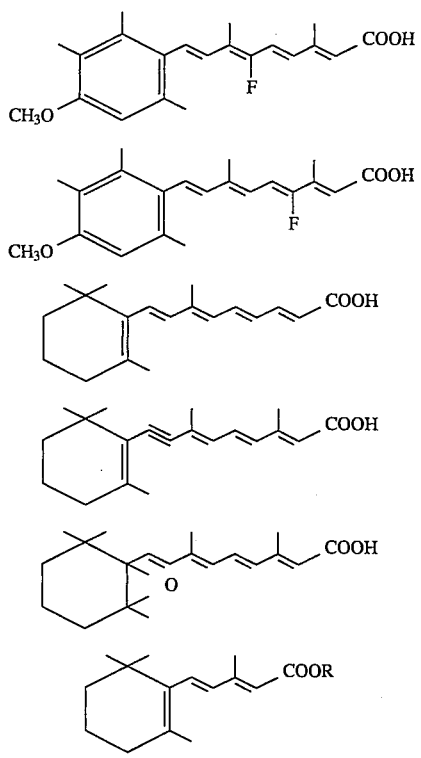

and physiologically acceptable salts or esters thereof.

7. The method of claim 1, wherein said retinoid is a member selected from the group consisting of compounds of formula (II):

A⏤⏤⏤⏤R  (II)

in the all-trans or 13-cis form, wherein R is selected from the groups consisting of —CH$_2$OH, —CHO and

where X is a group selected from the group consisting of OH, OY, an amino group, and an amino group that is mono- or disubstituted with a lower alkyl group that has 1 to 6 carbon atoms, wherein Y is an alkyl group having 1 to 15 carbon atoms, and wherein A is selected from the group consisting of

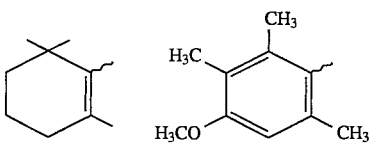

and pharmaceutically or cosmetically acceptable salts thereof.

8. The method of claim 1, wherein said physiologically acceptable media contain water or a solvent selected from the group consisting of glycol and dialkylene glycol alkyl ethers and is present in proportions of from 1 to 80% by weight relative to the total weight of each of the said components.

9. The method of claim 1, wherein the components are applied to the scalp intermittently such that component (B) is applied before and after component (A).

10. The process of claim 1, wherein the components are applied intermittently such that component (B) is applied to the scalp following an interval of from about 1 minute to about 12 hours from the time of application of component (A).

11. A method for inducing and stimulating hair growth and for decreasing hair loss or for improving the appearance of the hair, said method comprising applying a first component (A) and a second component (B) to the scalp, successively or intermittently, each component being in lotion, thickened lotion or gel form, (a) said first component (A) comprising a physiologically acceptable medium and 0.001 to 2% by weight relative to the weight of component (A) of at least one retinoid selected from the group consisting of compounds of formula:

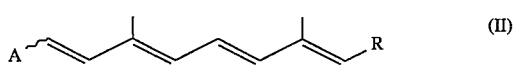

wherein

A is a substituent selected from the groups of formulae:

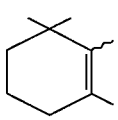 (IIIa)

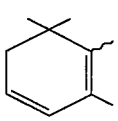 (IIIb)

-continued

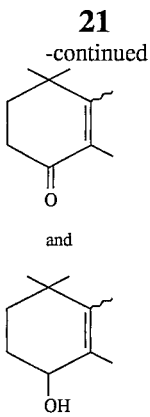

and wherein R is selected such that:

when A is a group of formula (IIIb), (IV) or (V), R is COOH;

when A is a group of formula (IIIa), R is selected from the group consisting of CHO, $CH_2OR_5$ in which $R_5$ is hydrogen or $C_1$–$C_4$ lower alkyl,

in which $R_6$ denotes $C_1$–$C_{16}$ linear or branched alkyl, $CH_2SR_7$ in which $R_7$ is hydrogen or methyl and

in which X is selected from the group consisting of
(i) OH,
(ii) $OR_6$ in which $R_8$ denotes a $C_1$–$C_4$ alkyl radical, an unsubstituted $C_1$–$C_4$ arylalkyl radical, a $C_1$–$C_4$ arylalkyl radical substituted on the aryl group, an unsubstituted $C_1$–$C_4$ arylcarboxyalkyl radical, a $C_1$–$C_4$ arylcarboxyalkyl radical substituted on the aryl group, or a $C_1$–$C_4$ hydroxyalkyl or $C_1$–$C_4$ amidoalkyl group;

(b) retinoids selected from the group consisting of compounds of formula (II) in which R is COOH, $CONHC_2H_5$ or $COOC_2H_5$ and A is selected from the group consisting of

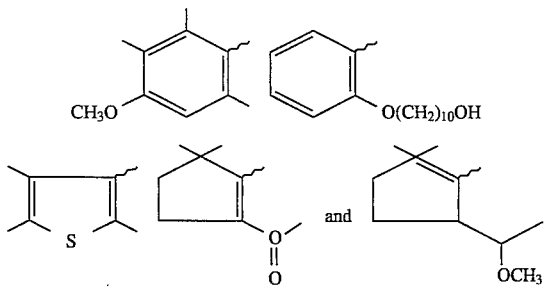

(c) retinoids selected from the group consisting of compounds of the formulae:

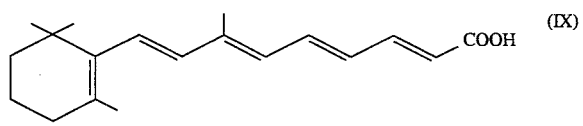

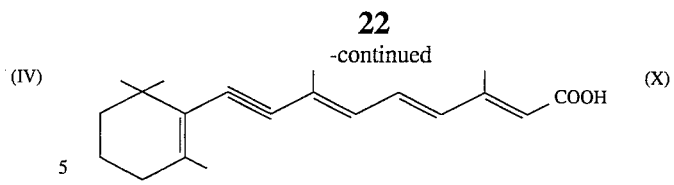

and the second component (B) comprises a physiologically acceptable medium and 0.1 to 3% by weight relative to the weight of component (B) of at least one pyrimidine derivative having the formula:

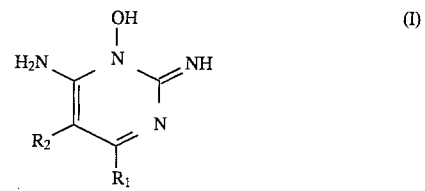

or an acid addition salt thereof, wherein $R_1$ represents a group having the formula

wherein each of $R_3$ and $R_4$ is a member selected from the group consisting of hydrogen, lower alkyl, alkenyl alkylaryl and cycloalkyl, the alkyl part of which is a lower alkyl radical, or $R_3$ and $R_4$ with the nitrogen to which each is bound, form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidino, hexahydrolazepinyl, heptamethylenimino, octamethylenimino, morpholine and 4-(lower alkyl)piperazinyl, and wherein $R_2$ is a member selected from the group consisting of hydrogen, lower alkyl, alkenyl, alkoxyalkyl, cycloalkyl, aryl, alkylaryl, arylalkyl, alkylarylalkyl, alkoxyarylalkyl and haloarylalkyl, the alkyl part of which is a lower alkyl radical.

12. The method of claim 1, wherein the components are applied to the scalp intermittently such that component (B) is applied before and after component (A).

13. The method of claim 1, wherein the components are applied intermittently such that component (B) is applied to the scalp following an interval of from about 1 minute to about 12 hours from the time of application of component (A).

14. A method for inducing and stimulating hair growth and for decreasing hair loss or for improving the appearance of the hair, said method comprising separately storing a first component (A) and a second component (B) and subsequently mixing said components and immediately applying said mixed components to the scalp, a) said first component (A) comprising a physiologically acceptable medium and 0.001 to 2% by weight of at least one retinoid selected from the group consisting of compounds of formula:

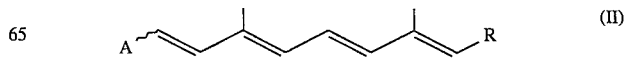

wherein

A is a substituent selected from groups of formulae:

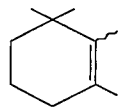
(IIIa)

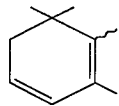
(IIIb)

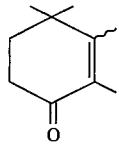
(IV)

and

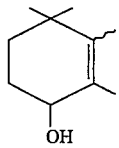
(V)

and wherein R is selected such that:

when A is a group of formula (IIIb), (IV) or (V), R is COOH;

when A is a group of formula (IIIa), R is selected from the group consisting of CHO, $CH_2OR_5$ in which $R_5$ is hydrogen or $C_1$–$C_4$ lower alkyl,

in which $R_6$ denotes $C_1$–$C_{16}$ linear or branched alkyl, $CH_2SR_7$ in which $R_7$ is hydrogen or methyl and

in which X is selected from the group consisting of
(i) OH,
(ii) $OR_8$ in which $R_8$ denotes a $C_1C_4$ alkyl radical, an unsubstituted $C_1C_4$ arylalkyl radical, a $C_1C_4$ arylalkyl radical substituted on the aryl group, an unsubstituted $C_1$–$C_4$ arylcarboxyalkyl radical, a $C_1$–$C_4$ arylcarboxyalkyl radical substituted on the aryl group, or a $C_1$–$C_4$ hydroxyalkyl or $C_2$–$C_4$ amidoalkyl group;

(b) retinoids selected from the group consisting of compounds of formula (II) in which R is COOH, $CONHC_2H_5$ or $COOC_2H_5$ and A is selected from the group consisting of

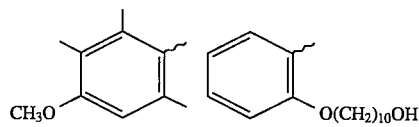

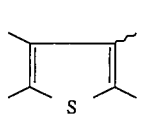
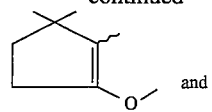
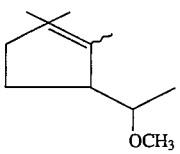 and (c) retinoids selected from the group consisting of compounds of the formulae:

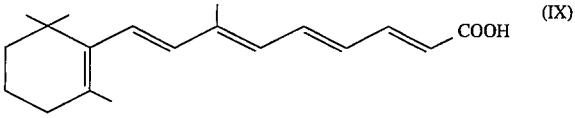
(IX)

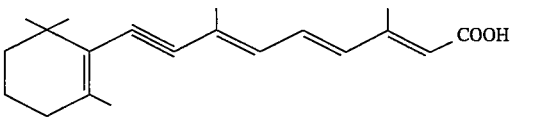
(X)

and (b) said second component (B) comprising a physiologically acceptable medium and an effective amount of at least one pyrimidine derivative having the formula:

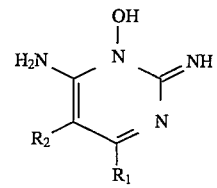
(I)

as well as acid addition salts thereof, wherein $R_1$ represents a group having the formula

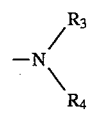
(II)

wherein $R_3$ and $R_4$ are selected from the group consisting of hydrogen, lower alkyl, alkenyl, alkylaryl and cycloalkyl, the alkyl part of which is a lower alkyl radical, or $R_3$ and $R_4$ with the nitrogen to which each is bound, form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidino, hexahydrolazepinyl, heptamethylenimino, octa-methylenimino, morpholine and 4-(lower alkyl)piperazinyl, and wherein $R_2$ is a member selected from the group consisting of hydrogen, lower alkyl, alkenyl, alkoxyalkyl, cycloalkyl, aryl, alkylaryl, arylalkyl, alkylarylalkyl, alkoxyarylalkyl and haloarylalkyl, the alkyl part of which is a lower alkyl radical.

15. A method for inducing and stimulating hair growth and for decreasing hair loss and for improving the appearance of the hair, comprising applying first and second components to the scalp, successively or intermittently, in separate steps, each component being in lotion, thickened lotion or gel form, the first component (A) comprising a physiologically acceptable medium and 0.001 to 2% by weight relative to the weight of component (A) of all trans retinoic acid and the second component (B) comprising a physiologically acceptable medium and 0.1 to 3% by weight relative to the weight of component (B) of minoxidil.

16. A method for inducing and simulating hair growth and for decreasing hair loss or for improving the appearance of the hair, comprising applying first and second components to the scalp, successively or intermittently, each component being in lotion, thickened lotion or gel form, wherein the first component (A) comprises a physiologically acceptable medium and 0.001 to 2% by weight relative to the weight of component (A) of at least one retinoid selected from the group consisting of retinal, retinol, retinyl acetate, propionate and palmitate, retinoic acid in all-trans, 13-cis, 9-cis, 11-cis or 9,13-dicis forms of retinoic acid, the corresponding zinc retinoates and quaternary ammonium retinoates of formula:

(VII)

in which X denotes an all-trans- or 13-cis-retinoate radical and $R_{13}$, $R_{14}$, $R_{15}$ $R_{16}$ are either (i), (ii) or (iii), wherein (i) $R_{13}$, $R_{14}$ and $R_{15}$, which may be identical or different, denote a $C_1$–$C_4$ linear alkyl group which can bear one or more hydroxyl group(s) in the chain, $R_{16}$ denotes a $C_{12}$–$C_{18}$ linear alkenyl or alkyl;

(ii) $R_{15}$ denotes a group:

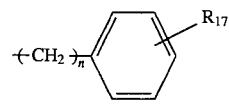

in which:

n equals 0 or 1, $R_{17}$ denotes a hydrogen or halogen atom, a hydroxyl group, a $C_1$–$C_{18}$ hydroxyalkyl or alkyl group or a $C_2$–$C_{18}$ acyl group;

$R_{13}$, $R_{14}$ and $R_{15}$ having the meanings stated under (i)

(iii) $R_{13}$ or $R_{14}$ can form an aliphatic heterocycle optionally containing an oxygen atom, a nitrogen atom or a sulphur atom;

$R_{15}$ or $R_{16}$ having the meanings stated under (i) and (ii), all-trans-retinoyloxyacetamide, the mixture of 2-hydroxy-1-propyl and 1-hydroxy-2-propyl all-trans-retinoates, 2-hydroxy-ethyl all-trans-retinoate, 4-nitrobenzyl all-trans-retinoate, benzyl all-trans-retinoate, 4-(all-trans-retinoyloxy-acetyl)catechol, 2-cyclohexylethyl all-trans-retinoate, 10-carboxymethyldecyl all-trans-retinoate, 4-hydroxybutyl all-trans-retinoate, cholesteryl all-trans-retinoate, 4-bromobenzyl all-trans-retinoate, cholesteryl all-trans-retinoyloxyacetate, all-trans-retinoyloxyacetyl-benzene, 4-(all-trans-retinoyloxyacetyl) bromobenzene, 4-(all-trans-retinoyloxyacetyl)nitrobenzene, 4-(all-trans-retinoyloxyacetyl)-benzonitrile, all-trans-retinoyloxyacetyl-2,4-dichlorobenzene, N-(all-trans-retinoyloxy)-phthalimide, N-(all-trans-retinoyloxy)-succinimide, 4-(all-trans-retinoyloxyacetyl)methoxybenzene, 4-(all-trans-retinoyloxyacetyl)phenol, 4-(all-trans-retinoyloxyacetyl)-3,4,5-trimethoxybenzene, 4-(all-trans-retinoyloxyacetyl)-2,4,6-trimethylbenzene, 4-(all-trans-retinoyloxyacetyl)-toluene, 4-(all-trans-retinoyloxyacetyl)ethoxybenzene, 4-(all-trans-retinoyloxyacetyl)acetoxybenzene, 4-(all-trans-retinoyloxyacetyl)naphthalene, 4-(all-trans-retinoyloxyacetyl)biphenyl, 4-(all-trans-retinoyloxyacetyl)-2,5-dimethoxybenzene, 1-(all-trans-retinoyloxyacetyl)-2,4-dimethylbenzene, 1-(all-trans-retinoyloxyacetyl)-3,4-diacetoxybenzene;

and the second component (B) comprises a physiologically acceptable medium and 0.1 to 3% by weight relative to the weight of component (B) of at least one pyrimidine derivative having the formula:

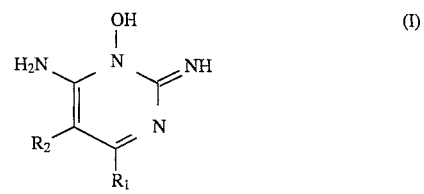
(I)

or an acid addition salt thereof, wherein $R_1$ represents a group having the formula

(II)

wherein each of $R_3$ and $R_4$ is a member selected from the group consisting of hydrogen, lower alkyl, alkenyl, alkylaryl and cycloalkyl, the alkyl part of which is a lower alkyl radical, or $R_3$ and $R_4$ with the nitrogen to which each is bound, form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidino, hexahydrolazepinyl, heptamethylenimino, octamethylenimino, morpholine and 4-(lower alkyl)piperazinyl, and wherein $R_2$ is a member selected from the group consisting of hydrogen, lower alkyl, alkenyl, alkoxyalkyl, cycloalkyl, aryl, alkylaryl, arylalkyl, alkylarylalkyl, alkoxyarylalkyl and haloarylalkyl, the alkyl part of which is a lower alkyl radical.

17. A method for inducing and stimulating hair growth and for decreasing hair loss or for improving the appearance of the hair, comprising applying first and second components to the scalp, successively or intermittently, each component being in lotion, thickened lotion or gel form, wherein the first component (A) comprises a physiologically acceptable medium and 0.001 to 2% by weight relative to the weight of component (A) of at least retinoic acid and the second component (B) comprises a physiologically acceptable medium and 0.1 to 3% by weight relative to the weight of component (B) of at least one pyrimidine derivative having the formula:

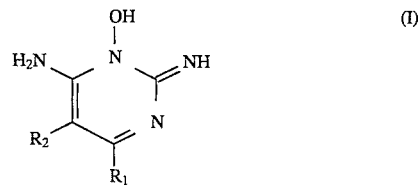
(I)

or an acid addition salt thereof, wherein $R_1$ represents a group having the formula

(II)

wherein each of $R_3$ and $R_4$ is a member selected from the group consisting of hydrogen, lower alkyl, alkenyl, alkylaryl and cycloalkyl, the alkyl part of which is a lower alkyl radical, or $R_3$ and $R_4$ with the nitrogen to which each is bound, form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidino, hexahydrolazepinyl, heptamethylenimino, octamethylenimino, morpholine and 4-(lower alkyl)piperazinyl, and wherein $R_2$ is a member selected from the group consisting of hydrogen, lower alkyl, alkenyl, alkoxyalkyl, cycloalkyl, aryl, alkylaryl, arylalkyl, alkylarylalkyl, alkoxyarylalkyl and haloarylalkyl, the alkyl part of which is a lower alkyl radical.

18. Method according to claim 17, wherein the retinoic acid is selected from the group consisting of 13-cis, 9-cis, 11-cis and 9,13-dicis retinoic acid.

19. The method of claim 17, wherein said physiologically acceptable media contain water or a solvent selected from the group consisting of glycol and dialkylene glycol alkyl ethers and is present in proportions of from 1 to 80% by weight relative to the total weight of each of said components.

20. A method for inducing and stimulating hair growth and for decreasing hair loss or for improving the appearance of the hair, comprising applying first and second components to the scalp, successively or intermittently, each component being in lotion, thickened lotion or gel form, wherein the first component (A) comprises a physiologically acceptable medium and 0.001 to 2% by weight relative to the weight of component (A) of at least all trans retinoic acid and the second component (B) comprises a physiologically acceptable medium and 0.1 to 3% by weight relative to the weight of component (B) of at least one pyrimidine derivative having the formula:

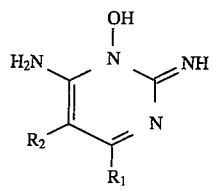

or an acid addition salt thereof, wherein $R_1$ represents a group having the formula

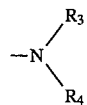

wherein each of $R_3$ and $R_4$ is a member selected from the group consisting of hydrogen, lower alkyl, alkenyl, alkylaryl and cycloalkyl, the alkyl part of which is a lower alkyl radical, or $R_3$ and $R_4$ with the nitrogen to which each is bound, form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidino, hexahydrolazepinyl, heptamethylenimino, octamethylenimino, morpholine and 4-(lower alkyl)piperazinyl, and wherein $R_2$ is a member selected from the group consisting of hydrogen, lower alkyl, alkenyl, alkoxyalkyl, cycloalkyl aryl, alkylaryl, arylalkyl, alkylarylalkyl, alkoxyarylalkyl and haloarylalkyl, the alkyl part of which is a lower alkyl radical.

21. The method of claim 20, wherein said physiologically acceptable media contain water or a solvent selected from the group consisting of glycol and dialkylene glycol alkyl ethers and is present in proportions of from 1 to 80% by weight relative to the total weight of each of the said components.

22. A method for inducing and stimulating hair growth and for decreasing hair loss or for improving the appearance of the hair, comprising applying first and second component to the scalp, successively or intermittently, each component being in lotion, thickened lotion or gel form, wherein the first component (A) comprises a physiologically acceptable medium and 0.001 to 2% by weight relative to the weight of component (A) of at least retinoic acid and the second component (B) comprises a physiologically acceptable medium and 0.1 to 3% by weight relative to the weight of component (B) of at least minoxidil.

23. Method according to claim 22, wherein the retinoic acid is selected from the group consisting of 13-cis, 9-cis, 11-cis and 9,13-dicis retinoic acid.

24. The method of claim 22, wherein said physiologically acceptable media contain water or a solvent selected from the group consisting of glycol and dialkylene glycol alkyl ethers and is present in proportions of from 1 to 80% by weight relative to the total weight of each of the said components.

25. A method for inducing and stimulating hair growth and for decreasing hair loss or for improving the appearance of the hair, comprising applying first and second component to the scalp, successively or intermittently, each component being in lotion, thickened lotion or gel form, wherein the first component (A) comprises a physiologically acceptable medium and 0.001 to 2% by weight relative to the weight of component (A) of at least all trans retinoic acid and the second component (B) comprises a physiologically acceptable medium and 0.1 to 3% by weight relative to the weight of component (B) of at least minoxidil.

26. The method of claim 25, wherein said physiologically acceptable media contain water or a solvent selected from the group consisting of glycol and dialkylene glycol alkyl ethers and is present in proportions of from 1 to 80% by weight relative to the total weight of each of the said components.

* * * * *